US012694987B2

(12) United States Patent
Shimuta

(10) Patent No.: US 12,694,987 B2
(45) Date of Patent: Jul. 28, 2026

(54) METHOD OF ESTIMATING GLUCOSE METABOLIC CAPACITY

(71) Applicant: Murata Manufacturing Co., Ltd., Nagaokakyo (JP)

(72) Inventor: Toru Shimuta, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 179 days.

(21) Appl. No.: 18/739,652

(22) Filed: Jun. 11, 2024

(65) Prior Publication Data

US 2024/0331876 A1 Oct. 3, 2024

Related U.S. Application Data

(63) Continuation of application No. PCT/JP2022/045103, filed on Dec. 7, 2022.

(30) Foreign Application Priority Data

Jan. 7, 2022 (JP) ................................. 2022-001358
Feb. 8, 2022 (JP) ................................. 2022-017760

(51) Int. Cl.
*G16H 50/30* (2018.01)
*G16H 10/60* (2018.01)

(52) U.S. Cl.
CPC ............. *G16H 50/30* (2018.01); *G16H 10/60* (2018.01)

(58) Field of Classification Search
None
See application file for complete search history.

(56) References Cited

U.S. PATENT DOCUMENTS

| | | | |
|---|---|---|---|
| 7,542,800 B2 | 6/2009 | Libbus et al. | |
| 8,452,398 B2 | 5/2013 | Libbus et al. | |
| 10,262,760 B2 * | 4/2019 | Granov | A61B 5/107 |
| 10,426,386 B2 | 10/2019 | Ishizawa et al. | |
| 10,617,310 B2 | 4/2020 | Amagasa et al. | |
| 10,624,546 B2 * | 4/2020 | Costa | A61B 5/0265 |
| 10,813,561 B2 | 10/2020 | Kwon et al. | |
| 10,856,783 B2 | 12/2020 | Ajima | |

(Continued)

FOREIGN PATENT DOCUMENTS

| | | |
|---|---|---|
| JP | S5283493 U | 6/1977 |
| JP | H08-080287 A | 3/1996 |

(Continued)

OTHER PUBLICATIONS

Zhang et al., "A Noninvasive Blood Glucose Monitoring System Based on Smartphone PPG Signal Processing and Machine Learning," IEEE Transactions on Industrial Informatics, vol. 16, No. 11, Nov. 2020. (Year: 2020).*

(Continued)

*Primary Examiner* — Michael Fuelling
(74) *Attorney, Agent, or Firm* — ArentFox Schiff LLP

(57) ABSTRACT

A biological information measurement system and method is provided that measures a peripheral hemodynamic index value of a user before an event that affects a blood glucose level of the user and a peripheral hemodynamic index value of the user after the event, and estimates a glucose metabolic capacity of the user from a change in the peripheral hemodynamic index values measured before and after the event.

8 Claims, 16 Drawing Sheets

(56)                    References Cited

U.S. PATENT DOCUMENTS

| | | | |
|---|---|---|---|
| 11,471,072 B2 * | 10/2022 | Lynde | A61B 5/024 |
| 11,864,889 B2 | 1/2024 | Ajima | |
| 2006/0224188 A1 | 10/2006 | Libbus et al. | |
| 2009/0228060 A1 | 9/2009 | Libbus et al. | |
| 2013/0253616 A1 | 9/2013 | Libbus et al. | |
| 2015/0366473 A1 * | 12/2015 | Shimuta | A61B 5/02125 |
| | | | 600/479 |
| 2017/0209055 A1 | 7/2017 | Pantelopoulos et al. | |
| 2018/0008175 A1 | 1/2018 | Ishizawa et al. | |
| 2018/0110474 A1 * | 4/2018 | Yamada | A61B 5/7278 |
| 2018/0177413 A1 | 6/2018 | Kwon et al. | |
| 2018/0192889 A1 | 7/2018 | Amagasa et al. | |
| 2019/0183365 A1 * | 6/2019 | Liu | A61B 7/04 |
| 2020/0129123 A1 | 4/2020 | Ajima | |
| 2021/0038133 A1 | 2/2021 | Ajima | |
| 2021/0233656 A1 * | 7/2021 | Tran | G06Q 10/40 |
| 2022/0414865 A1 * | 12/2022 | Itu | G06T 7/11 |
| 2024/0081694 A1 | 3/2024 | Ajima | |

FOREIGN PATENT DOCUMENTS

| | | | |
|---|---|---|---|
| JP | H09-135819 | A | 5/1997 |
| JP | 2003-190123 | A | 7/2003 |
| JP | 2006-006897 | A | 1/2006 |
| JP | 2017-029651 | A | 2/2017 |
| JP | 2018-102906 | A | 7/2018 |
| JP | 2008-534218 | A | 8/2018 |
| JP | 2019-109218 | A | 7/2019 |
| JP | 6789142 | B2 | 11/2020 |
| WO | 2016/147795 | A1 | 9/2016 |
| WO | 2016/174839 | A1 | 11/2016 |

OTHER PUBLICATIONS

U.S. Food and Drug Administration, "Do Not Use Smartwatches or Smart Rings to Measure Blood Glucose Levels: FDA Safety Communication," FDA.gov, Feb. 21, 2024. (Year: 2024).*

International Search Report received for PCT Patent Application No. PCT/JP2022/045103, mailed on Feb. 28, 2023, 2 pages (English Translation Only).

* cited by examiner

TIME AFTER GLUCOSE TOLERANCE TEST [min]

METHOD OF ESTIMATING GLUCOSE METABOLIC CAPACITY

CROSS REFERENCE TO RELATED APPLICATIONS

This application is a continuation of International Application No. PCT/JP2022/045103, filed Dec. 7, 2022, which claims priority to Japanese Patent Application Nos. 2022-001358, filed Jan. 7, 2022, and 2022-017760, filed Feb. 8, 2022, the entire contents of each of which are hereby incorporated in their entirety.

TECHNICAL FIELD

The present disclosure relates to a method of estimating a glucose metabolic capacity of a user.

BACKGROUND OF THE INVENTION

The pulse wave signal is a signal in which a change in volume of a blood vessel generated by the heart sending out blood through the blood vessel is captured as a waveform. For example, PCT International application No. 2016/174839 describes a method of estimating a state of glucose metabolism of a user (subject) from an index calculated based on a pulse wave signal measured at peripheral body parts of the user. Examples of the index calculated based on the pulse wave signal include (1) a pulse wave velocity (PWV) of a forward wave, (2) a magnitude of a reflected wave of the pulse wave, (3) a time difference between the forward wave and the reflected wave of the pulse wave, and (4) an augmentation index (AI) represented as the ratio between magnitudes of the forward wave and the reflected wave of the pulse wave.

However, since the PWV is calculated based on the propagation time difference between the pulse wave signals measured at two body parts (for example, the arm and the ankle) of the user and the distance between the two body parts, it may be necessary to physically restrain the user to some extent in order to calculate the PWV. Therefore, it is difficult to easily measure the PWV without physically restraining the user.

In addition, the magnitude of the reflected wave of the pulse wave can be relatively easily measured at a body part of the artery of the user, but the shape of the reflected wave of the pulse wave may change at a body part of the peripheral blood vessel of the user depending on the physical condition or the individual difference such as the blood pressure, and thus a problem may occur in that it is difficult to detect the reflected wave. The same problem may occur in a case of measuring the time difference between the forward wave and the reflected wave of the pulse wave or measuring the AI represented as the ratio between the magnitudes of the forward wave and the reflected wave of the pulse wave.

SUMMARY OF THE INVENTION

Accordingly, it is an object of the present disclosure to solve the above-described problems and to estimate a glucose metabolic capacity of a user with high accuracy by a simple measurement.

According to an exemplary aspect, a method to be executed by a biological information measurement system according to the present disclosure is provided that includes measuring a peripheral hemodynamic index value of a user before an event that affects a blood glucose level of the user and a peripheral hemodynamic index value of the user after the event, and estimating a glucose metabolic capacity of the user from a change in the peripheral hemodynamic index values measured before and after the event.

According to the exemplary method of the present disclosure, the glucose metabolic capacity can be estimated in a non-invasive and simple manner.

BRIEF DESCRIPTION OF DRAWINGS

In the descriptions that follow, like parts are marked throughout the specification and drawings with the same numerals, respectively. The drawings are not necessarily drawn to scale and certain drawings may be shown in exaggerated or generalized form in the interest of clarity and conciseness. The disclosure itself, however, as well as a mode of use, further features and advances thereof, will be understood by reference to the following detailed description of illustrative implementations of the disclosure when read in conjunction with reference to the accompanying drawings, wherein.

DETAILED DESCRIPTION

Figure 1:
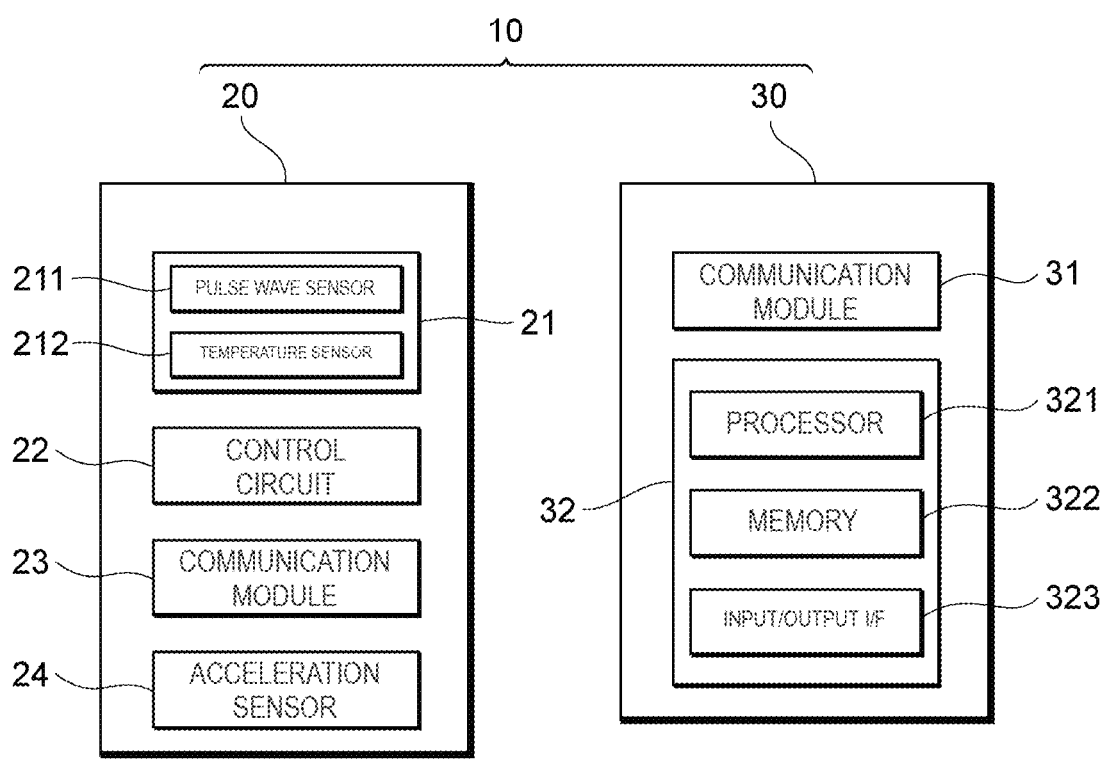
FIG. 1 is a diagram illustrating a configuration of a biological information measurement system in accordance with exemplary aspects of the present disclosure.

Hereinafter, exemplary aspects of the present disclosure will be described with reference to the accompanying drawings. For purposes of this disclosure, the same reference numerals denote the same constituent elements, and redundant description thereof will be omitted.

FIG. 1 is a diagram illustrating a configuration of a biological information measurement system 10 according to an exemplary aspect of the present disclosure. The biological information measurement system 10 includes a sensing device 20 that is configured to measure biological information of a user (e.g., a subject) and a computer 30 that is configured to be communicable with the sensing device 20.

The sensing device 20 is, for example, a wearable device having a structure that can be mounted on a peripheral body part (for example, a finger) of a user. The sensing device 20 includes a biosensor 21 that is configured to measure biological information from a peripheral body part (for example, a finger) of the user, a control circuit 22 that is configured to control an operation of the biosensor 21, a communication module 23 that is configured to transmit a measurement result of the sensing device 20 to the computer 30 via a wireless line or a wired line, and an acceleration sensor 24 that is configured to measure a movement acceleration of the sensing device 20.

The biosensor 21 includes, for example, a pulse wave sensor 211 that is configured to measure an index value indicating the peripheral blood pressure of the user and a temperature sensor 212 that is configured to measure the skin temperature of the peripheral body part of the user. The peripheral blood pressure in the present disclosure denotes the blood pressure of a peripheral capillary or an arteriole. As the pulse wave sensor 211, for example, a photoplethysmographic sensor or a piezoelectric pulse wave sensor can be used. For example, a reflective photoplethysmographic sensor irradiates a body surface of the user with infrared rays, red light, or light having a green wavelength, and measures light reflected on the body surface of the user by using a photodiode or a phototransistor. The arterial blood contains oxidized hemoglobin and has a property of absorbing incident light, and thus the pulse wave signal can be measured by sensing the blood flow rate (change in volume of the blood vessel) that changes with the pulsation of the heart in a time series.

The communication module 23 is configured to transmit the measurement result of the sensing device 20 (for example, a pulse wave signal measured by the pulse wave sensor 211, a temperature value measured by the temperature sensor 212, and a movement acceleration of the sensing device 20 measured by the acceleration sensor 24) to the computer 30 via a wireless line or a wired line.

The acceleration sensor 24 is configured to measure the movement acceleration of the sensing device 20 when the user changes the posture in order to measure the pulse wave signal. The reason for measuring the movement acceleration of the sensing device 20 will be described below.

The computer 30 is, for example, a multifunctional mobile phone, such as a smartphone or a general-purpose computer (for example, a notebook personal computer, a desktop personal computer, a tablet terminal, or a server computer). The computer 30 includes a communication module 31 that is configured to receive the measurement result of the biosensor 21 from the sensing device 20 via a wireless line or a wired line, and a signal processing device 32 that is configured to perform processing of estimating biological information of a user from the measurement result of the biosensor 21. The signal processing device 32 includes a processor 321, a memory 322, and an input/output interface 323.

The signal processing device 32 is configured to calculate, for example, a pulse wave feature quantity from the pulse wave signal measured by the pulse wave sensor 211 and can estimate the blood pressure, the blood glucose value, the vascular resistance, the peripheral blood pressure, the peripheral blood flow rate, or the arteriosclerosis level of the user based on the pulse wave feature quantity. In addition, the signal processing device 32 can be configured to estimate the heart rate (pulse rate) by determining the variation period from the pulse wave signal measured by the pulse wave sensor 211. In addition, the signal processing device 32 is configured to estimate the index value of the autonomic nerve function by performing power spectrum analysis on the frequency component of the periodic variation of the heartbeat.

Figure 2:
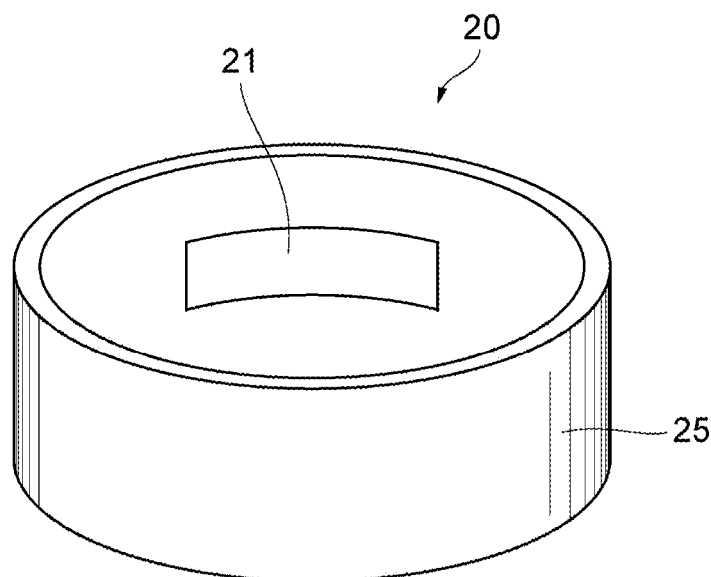
FIG. 2 is a diagram illustrating an external configuration of a sensing device in accordance with exemplary aspects of the present disclosure.

FIG. 2 is a diagram illustrating an external configuration of the sensing device 20 according to an aspect of the present disclosure. The sensing device 20 includes a housing 25 having a ring shape that is configured to be mountable to a finger of a user. For example, the housing 25 has a hollow cylindrical shape in the example illustrated in FIG. 2. The biosensor 21 is attached to an inner peripheral surface (an inner surface of the hollow cylinder) of the housing 25 such that an inner surface of the user's finger faces the biosensor 21 in a case where the sensing device 20 is mounted on the user's finger. It is noted that the shape of the housing 25 is not limited to the hollow cylindrical shape, and for example, may be a tubular shape that fits on the user's finger (for example, a finger cot shape) with or without a bottom (portion where the fingertip comes into contact with) of the cylindrical shape in alternative aspects.

Figure 3:
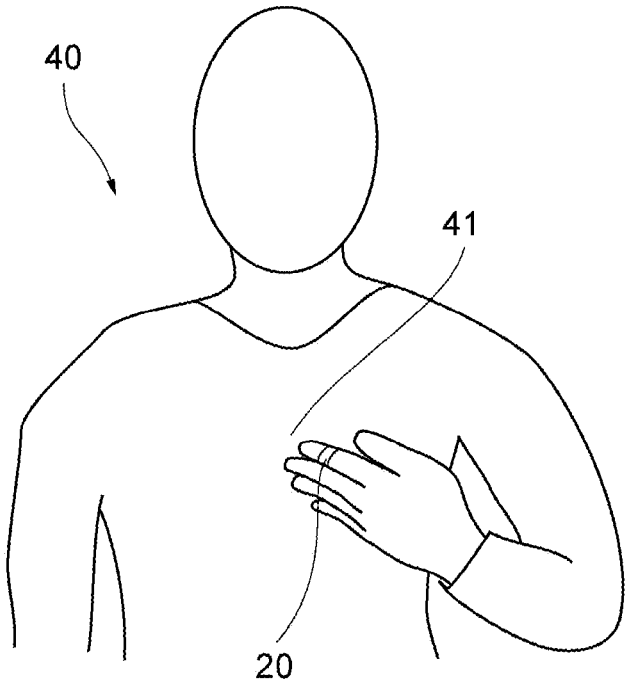
FIG. 3 is a diagram illustrating an example of a posture of a user in a case of measuring biological information in accordance with exemplary aspects of the present disclosure.

FIG. 3 illustrates an example of a posture of a user 40 in a case of measuring biological information. In this example, the user 40 measures the biological information from the finger of the user 40 in a state where the finger on which the sensing device 20 is mounted is stationary at the position of a heart 41. Note that the position (measurement position) of the sensing device 20 when measuring the biological information is not limited to the position of the heart 41 of the user 40, and may be, for example, the position of the face or the position of the abdomen of the user 40. In addition, the posture of the user 40 when measuring the biological information may be a sitting posture or a supine posture.

Figure 4:
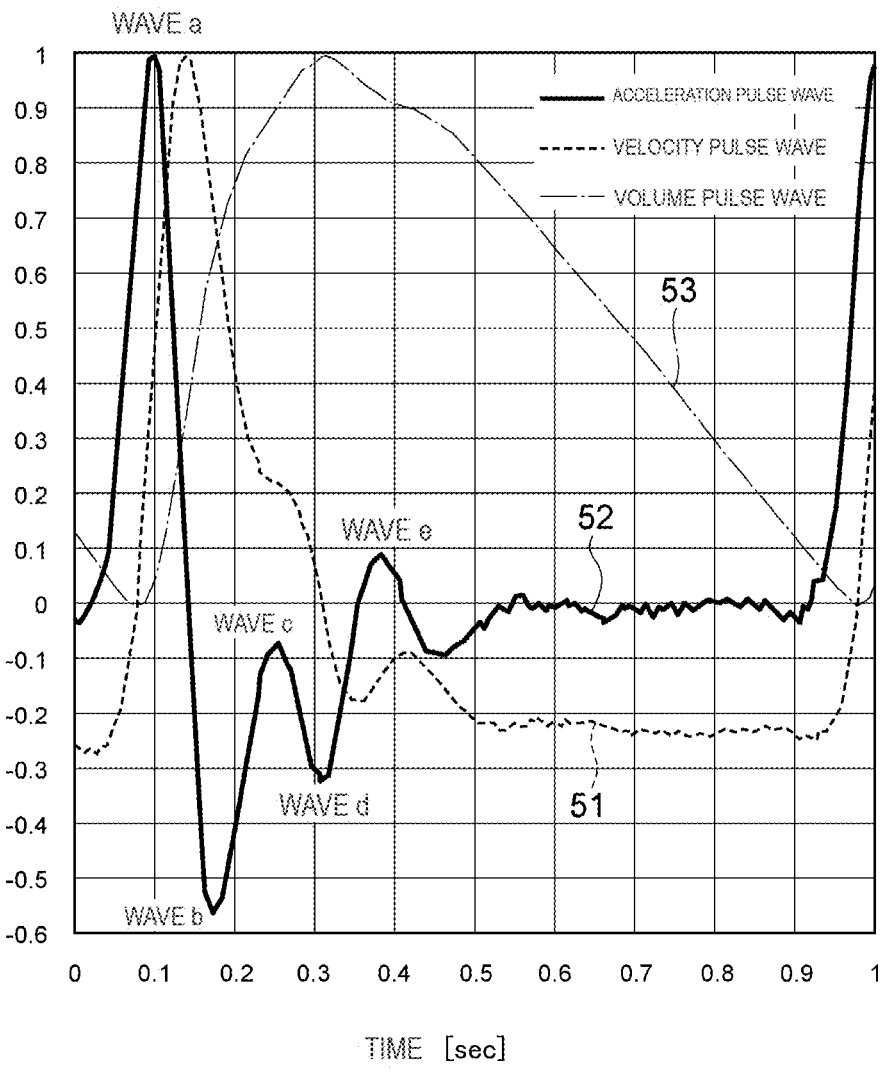
FIG. 4 is a diagram illustrating a pulse wave feature quantity in accordance with exemplary aspects of the present disclosure.

Next, the pulse wave feature quantity will be described with reference to FIG. 4. The reference numeral 51 denotes the velocity pulse wave signal obtained by performing first-order differentiation on the pulse wave signal. The reference numeral 52 denotes the acceleration pulse wave signal obtained by performing second-order differentiation on the pulse wave signal. The peaks (the relative maximum peaks and the relative minimum peaks) of the acceleration pulse wave signal 52 will also be referred to as a wave a, a wave b, a wave c, a wave d, and a wave e as illustrated in FIG. 4. The reference numeral 53 denotes the volume pulse wave signal. As the pulse wave feature quantity, for example, peak time differences of respective peaks (the wave a, the wave b, the wave c, the wave d, and wave e), a height of each peak, a ratio of the peak time difference of each peak to the pulse interval, a peak half width, a ratio between an area on the positive side and an area on the negative side with respect to a portion of the wave a to the wave e of the acceleration pulse wave signal 52, a degree of match between the measured pulse wave waveform and the template of the pulse wave waveform, and the like can be used. In addition, as the pulse wave feature quantity, not only the pulse wave feature quantity for each beat, but also an average value or a standard deviation of the pulse wave feature quantity from several beats to several tens of beats can be used.

Among the pulse wave feature quantities, the pulse wave feature quantity that is easily affected by the contact state or the pressing between the biosensor 21 and the skin is, for example, a feature quantity related to the signal intensity, such as the pulse wave height or the height of the wave a, the wave b, the wave c, the wave d, and the wave e of the acceleration pulse wave. As compared with such a pulse wave feature quantity, the pulse wave feature quantity that is less likely to be affected by the contact state or the pressing between the biosensor 21 and the skin is a pulse wave feature quantity related to time, such as the peak time of the wave a, the wave b, the wave c, the wave d, and the wave e. By calculating an index value indicating the degree of the peripheral blood flow rate or the degree of the peripheral blood pressure of the user from the pulse wave feature quantity related to time, the pulse wave feature quantity can be less likely to be affected by the contact state or the pressing between the biosensor 21 and the skin. In the present specification, an index indicating the degree of the peripheral blood flow rate or the degree of the peripheral blood pressure will be referred to as a peripheral hemodynamic index. Further, the blood flow rate denotes a peripheral blood flow rate unless otherwise specified.

Figure 5:
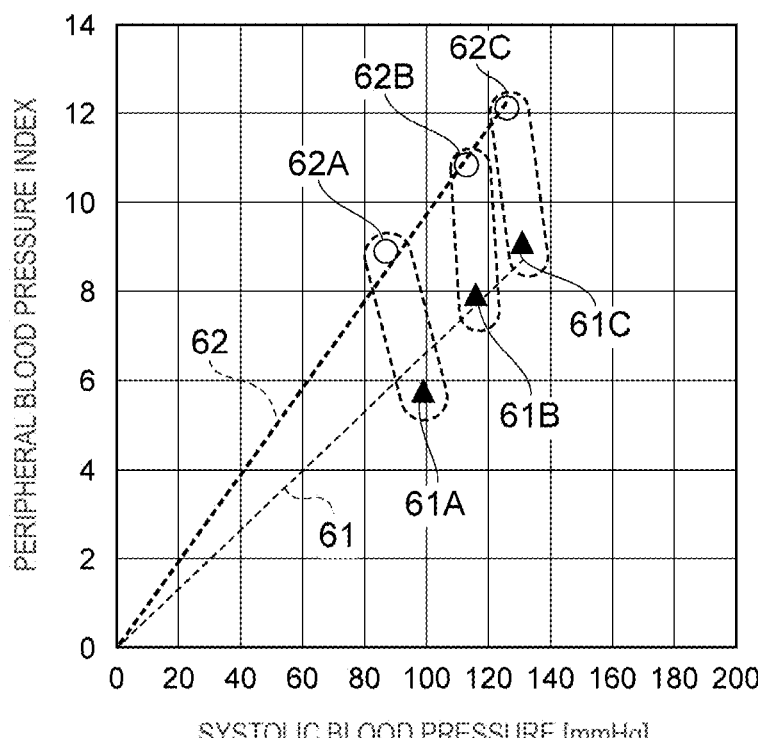
FIG. 5 is a graph showing a correlation between a peripheral blood pressure index value calculated from the pulse wave feature quantity with respect to time and a systolic blood pressure in accordance with exemplary aspects of the present disclosure.
Figure 6:
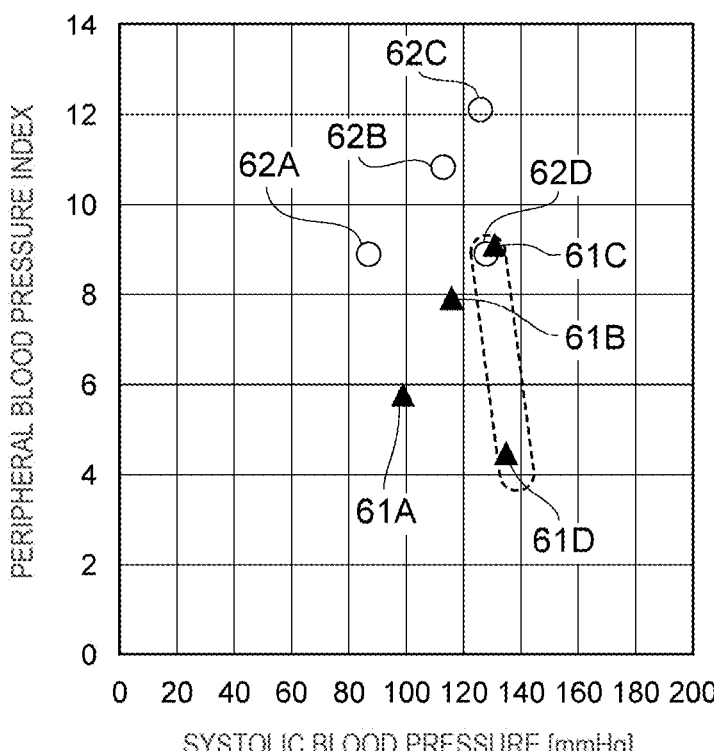
FIG. 6 is a graph showing a correlation between a peripheral blood pressure index value calculated from a pulse wave feature quantity with respect to time and a systolic blood pressure in accordance with exemplary aspects of the present disclosure.

FIGS. 5 and 6 show a correlation between the peripheral blood pressure index value calculated from the pulse wave feature quantity related to time and the systolic blood pressure (SBP) measured by the wrist-type cuff sphygmomanometer. In particular, FIG. 5 shows a graph in which the correlation between the systolic blood pressure and the peripheral blood pressure index is plotted in a case where the height of the measurement position (for example, a finger) from the heart is changed for each of two subjects A and B. Measurement points 61A, 61B, and 61C each denote the relationship between the peripheral blood pressure index value measured at the height of the forehead, the height of the chest, and the height of the navel of the subject A and the systolic blood pressure, and a graph 61 is obtained by the regression analysis of these measurement points 61A, 61B, and 61C. Measurement points 62A, 62B, and 62C each denote the relationship between the peripheral blood pressure index value measured at the height of the forehead, the height of the chest, and the height of the navel of the subject B and the systolic blood pressure, and a graph 62 is obtained by the regression analysis of these measurement points 62A, 62B, and 62C. In general, the peripheral blood pressure decreases with respect to the systolic blood pressure measured at the wrist due to the vascular resistance between the wrist and the periphery. When only the height of the measurement position from the heart is changed, the vascular resistance between the wrist and the periphery can be regarded as substantially constant, and thus the peripheral blood pressure is proportional to the systolic blood pressure at the wrist. FIG. 5 illustrates that the peripheral blood pressure index is substantially proportional to the systolic blood pressure when only the height of the measurement position from the heart is changed.

In FIG. 6, a measurement point 61D denotes a relationship between the peripheral blood pressure index value measured at the height of the chest of the subject A and the systolic blood pressure in a state where the vicinity of the measurement position (for example, a finger) of the subject A is cooled. Similarly, a measurement point 62D denotes a relationship between the peripheral blood pressure index value measured at the height of the chest of the subject B and the systolic blood pressure in a state where the vicinity of the measurement position (for example, a finger) of the subject B is cooled. It can be seen that, in the case where the vicinity of the measurement position is cooled, the systolic blood pressure is slightly increased and the peripheral blood pressure index is greatly decreased. The reason for this is considered that the blood vessel contracts due to the cooling and the vascular resistance is greatly increased, and as a result, the peripheral blood pressure is greatly decreased and the systolic blood pressure is increased.

The present inventor has examined a relationship between the change in the blood glucose value and the peripheral blood pressure index in a case where a glucose tolerance test (75 g OGTT) is performed by using the peripheral blood pressure index. A commercially available blood-collecting blood glucose self-measuring device is used to measure the blood glucose value.

Figure 7:
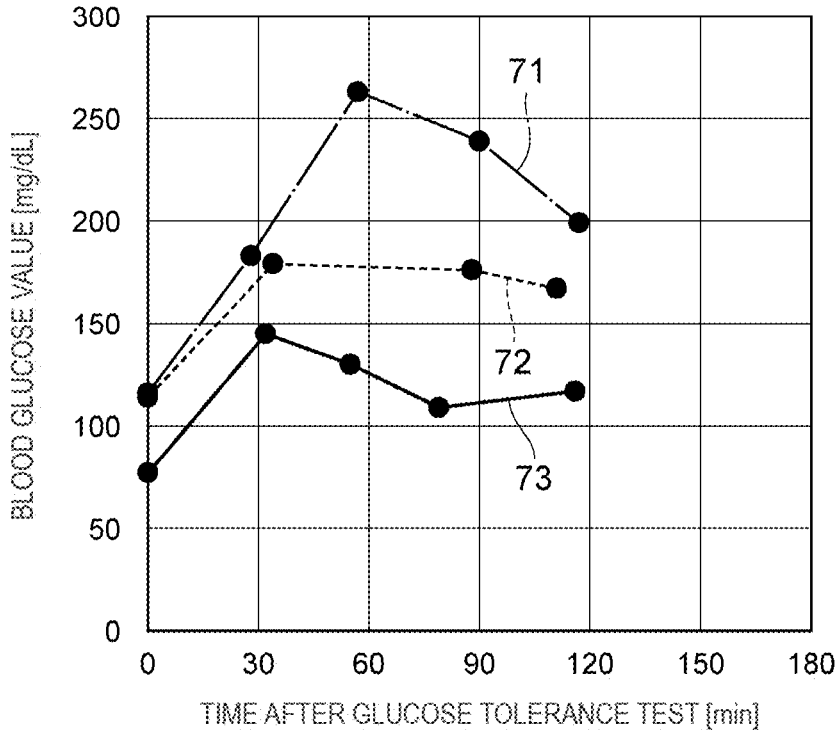
FIG. 7 is a graph showing a measurement result of a change in a blood glucose value over time after a glucose tolerance test in accordance with exemplary aspects of the present disclosure.
Figure 8:
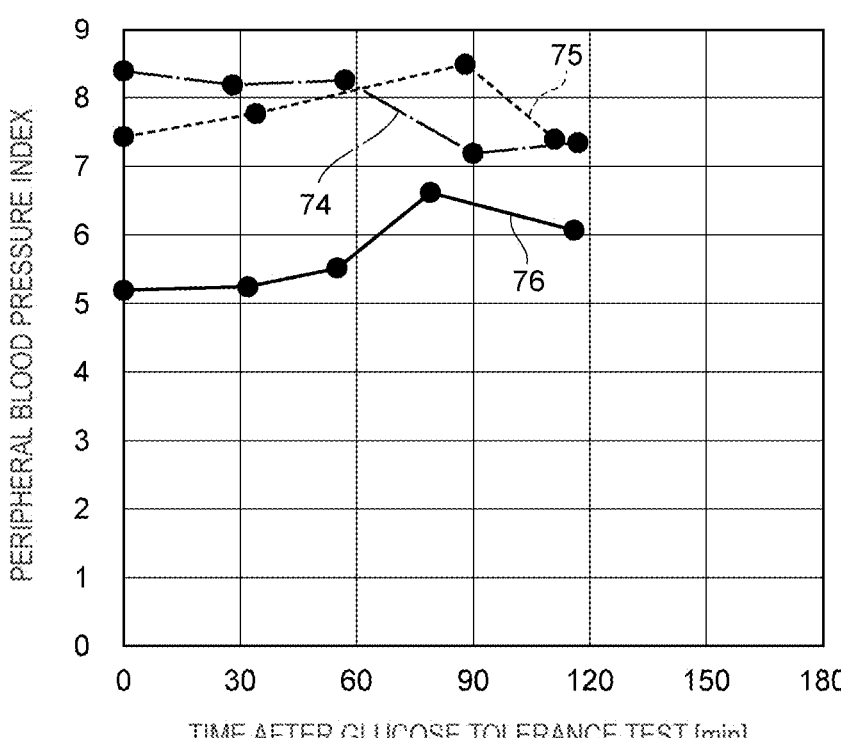
FIG. 8 is a graph showing a measurement result of a change in a peripheral blood pressure index over time after a glucose tolerance test in accordance with exemplary aspects of the present disclosure.

FIG. 7 shows the results of a change in the blood glucose value over time after the glucose tolerance test. Graphs 71, 72, and 73 respectively show a change in the blood glucose value over time after the glucose tolerance test measured with respect to the subjects C, D, and E. FIG. 8 shows the results of a change in the peripheral blood pressure index over time after the glucose tolerance test. Graphs 74, 75, and 76 respectively show a change in the peripheral blood pressure index over time after the glucose tolerance test measured with respect to the subjects C, D, and E. As illustrated in FIG. 7, the blood glucose value of the subject C is greatly increased and temporarily exceeds 250 mg/dL. Meanwhile, the change amounts and the maximum values of the blood glucose values of the subjects D and E are smaller than those of the subject C. In addition, as illustrated in FIG. 8, the peripheral blood pressure indices of the subjects D and E are increased, but the peripheral blood pressure index of the subject C is decreased.

The present inventor has calculated a rate of change in the measured value with reference to the measured value (the blood glucose value or the peripheral blood pressure index value) before the glucose tolerance test. Since the measurement of the blood glucose value and the peripheral blood pressure index value is intermittently performed and the measurement interval is not constant, a rate of change in the measured value is calculated according to Calculation Formula (1) below:

Math. 1

$$\sum \left( \left( (X_i + X_{i-1})/2 - X_0 \right) \times (t_i - t_{i-1}) \right)/(t_n - t_0)/X_0 \times 100[\%] \qquad (1)$$

Here, X denotes the measured value (the blood glucose value or the peripheral blood pressure index value). i denotes the measurement number (an integer of 1 to n) indicating the number of times of measurement of the measured value. X0 denotes the measured value before the glucose tolerance test. Xi denotes the measured value (measured value obtained in the i-th measurement) of a measurement number i. t0 denotes the start time of the glucose tolerance test ti denotes the measurement time of Xi.

Figure 9:
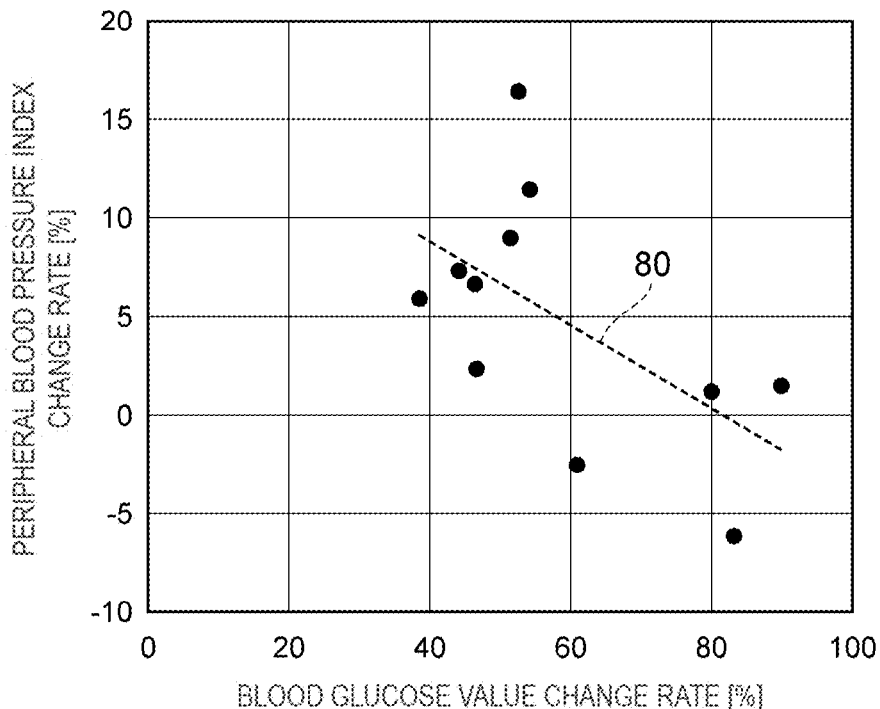
FIG. 9 is a graph of a peripheral blood pressure index change rate with respect to a blood glucose value change rate in accordance with exemplary aspects of the present disclosure.

FIG. 9 shows a graph 80 of a peripheral blood pressure index change rate with respect to a blood glucose value change rate. The graph 80 is obtained by the regression analysis of the measurement points of different subjects, and each measurement point denotes the relationship between the blood glucose value change rate and the peripheral blood pressure index change rate. Each of the blood glucose value change rate and the peripheral blood pressure index change rate is a change rate calculated according to Calculation Formula (1). As shown in the graph 80, the peripheral blood pressure index change rate decreases as the blood glucose value change rate increases. In diabetes, blood vessels are damaged due to a decrease in glucose metabolic capacity and a continued hyperglycemic state, and this results in a decrease in a vascular endothelial function. Accordingly, arteriosclerosis or peripheral vascular disorders progress in many cases. The vascular endothelial function is a function of a vascular endothelial cell. The vascular endothelial cell is a cell present in the innermost layer of a blood vessel and plays an important role in maintaining the state of health of the blood vessel. The vascular endothelial cells release a large number of vasoactive substances (factors that act on blood vessels) such as nitric oxide and endothelin, and perform contraction and relaxation (hardness and softness of blood vessels) of a blood vessel wall, adhesion of inflammatory cells to the blood vessel wall, regulation of blood vessel permeability, regulation of the coagulation/fibrinolytic system, and the like. It is presumed that, when the glucose metabolic capacity is decreased, the peripheral blood flow rate tends to decrease. However, since the absolute value of the blood flow rate is greatly changed depending on a meal, exercise, an outside air temperature, a blood pressure, and the like, it is difficult to find a clear correlation between the absolute value of the instantaneous blood flow rate and the glucose metabolic capacity.

Therefore, a method is provided according to an exemplary aspect for estimating the glucose metabolic capacity by focusing on a change in the peripheral blood flow rate or a change in the peripheral blood pressure instead of the absolute value of the peripheral blood flow rate. The vascular endothelial function includes contraction and relaxation of a blood vessel wall, and the capacity to regulate the blood flow (peripheral hemodynamic regulation capacity) is decreased in a case where the vascular endothelial function is decreased. It is presumed that the change in peripheral blood flow rate or the change in peripheral blood pressure is also decreased in a case in which the peripheral hemodynamic regulation capacity is decreased.

It is noted that the peripheral blood pressure index change rate calculated according to Calculation Formula (1) has been described as an example of the change in peripheral blood pressure, but examples of the change in peripheral blood pressure are not limited thereto, and for example, a maximum value of the peripheral blood pressure index change rate (peripheral blood pressure index change rate in which the absolute value of the peripheral blood pressure index change rate is maximized), a maximum value of the peripheral blood pressure index change amount (peripheral blood pressure index change amount in which the absolute value of the peripheral blood pressure index change amount is maximized), the peripheral blood pressure index change amount calculated using $(t_i-t_{i-1})/(t_n-t_0)$ in place of $(t_i-t_{i-1})/(t_n-t_0)/X_0$ in Calculation Formula (1), a dispersion (variation) in the peripheral blood pressure index change rate, a coefficient of variation, a time from the glucose tolerate having an extreme value, and a change pattern (classification of a change over time in the measured value as the shape of the figure) may be used alone or in combination. In addition, in order to accurately capture the change in the measured value, it is desirable to continuously perform measurement, but a measured value obtained by intermittent measurement or a measured value after a specified time (for example, after 120 minutes) from the glucose tolerance may be used.

The coefficient of determination of the graph 80 shown in FIG. 9 is about 0.33, and the degree of fit of the estimated regression formula is not a satisfactory value. It is considered that as one of the causes of the unsatisfactory coefficient of determination, the blood glucose value change rate caused by the glucose tolerance test is affected by the physical condition of the subject during the test, the food and drink taken within a few hours before the glucose tolerance test, and the like.

Figure 10:
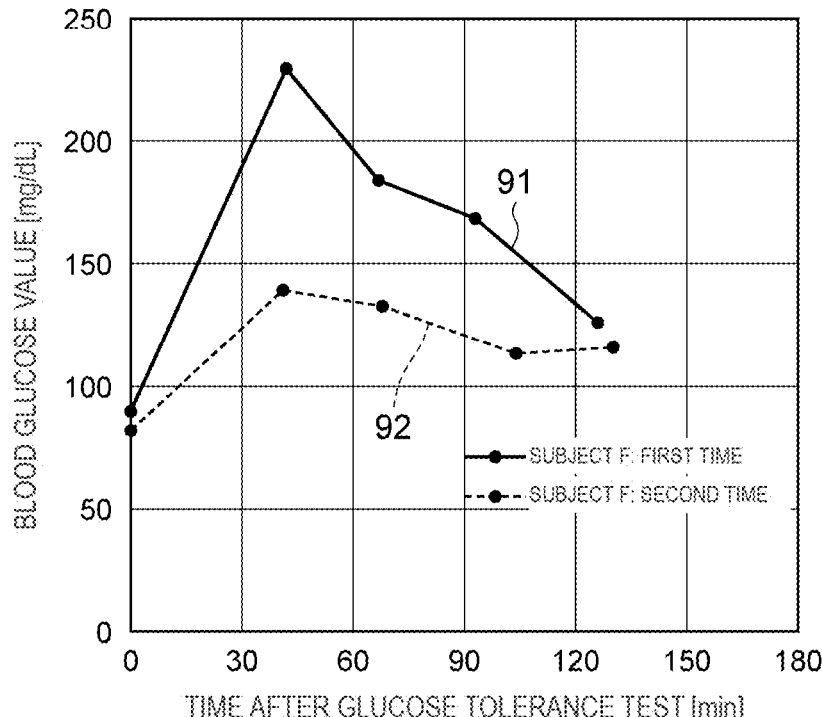
FIG. 10 is a graph showing a measurement result of a change in a blood glucose value over time after a glucose tolerance test in a case where the same subject undergoes the glucose tolerance test on different days in accordance with exemplary aspects of the present disclosure.

FIG. 10 shows the result of a change in the blood glucose value over time after the glucose tolerance test in a case where the same subject F undergoes the glucose tolerance test on different days. A graph 91 shows a change in the blood glucose value over time after the glucose tolerance test in a case where the subject F undergoes the first glucose tolerance test on a specified day. A graph 92 shows a change in the blood glucose value over time after the glucose tolerance test in a case where the subject F undergoes the second glucose tolerance test on a different day.

Figure 11:
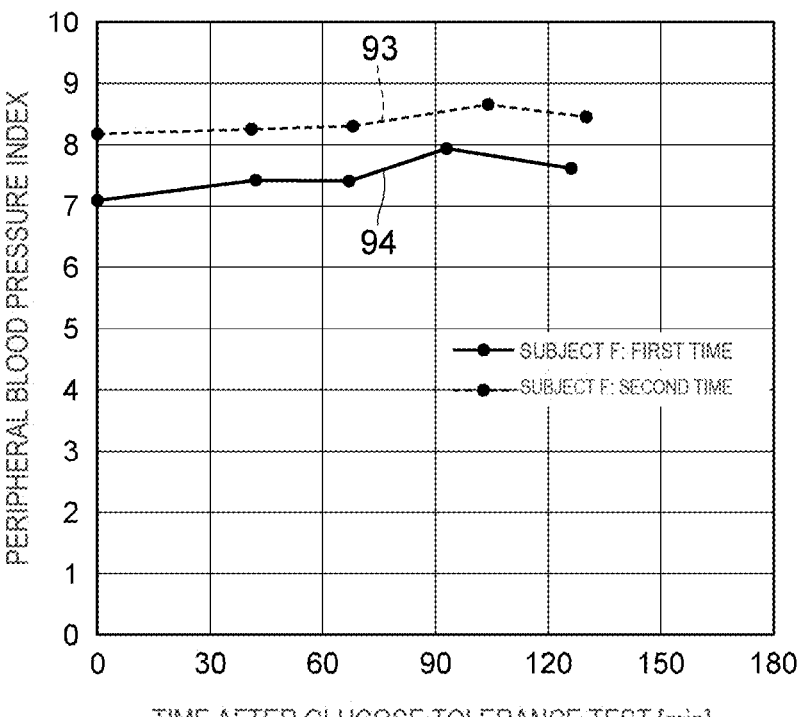
FIG. 11 is a graph showing a measurement result of a change in a peripheral blood pressure index value over time after a glucose tolerance test in a case where the same subject undergoes the glucose tolerance test on different days in accordance with exemplary aspects of the present disclosure.

FIG. 11 shows the result of a change in the peripheral blood pressure index value over time after the glucose tolerance test in a case where the same subject F undergoes the glucose tolerance test on different days. A graph 93 shows a change in the peripheral blood pressure index value over time after the glucose tolerance test in a case where the subject F undergoes the first glucose tolerance test on a specified day. A graph 94 shows a change in the peripheral blood pressure index value over time after the glucose tolerance test in a case where the subject F undergoes the second glucose tolerance test on a different day.

As shown in the results of FIG. 10, the change in the blood glucose value over time is large in the first glucose tolerance test, and the change in the blood glucose value over time is small in the second glucose tolerance test. The subject F undergoes measurement of the blood glucose value in the first glucose tolerance test after taking coffee a few hours before the glucose tolerance test, whereas the subject F undergoes measurement of the blood glucose value in the second glucose tolerance test without taking coffee. It is not clear to what extent the intake of coffee affects the change in the blood glucose value over time, but it can be seen that the change in the blood glucose value over time varies greatly depending on whether or not the subject takes coffee.

Figure 12:
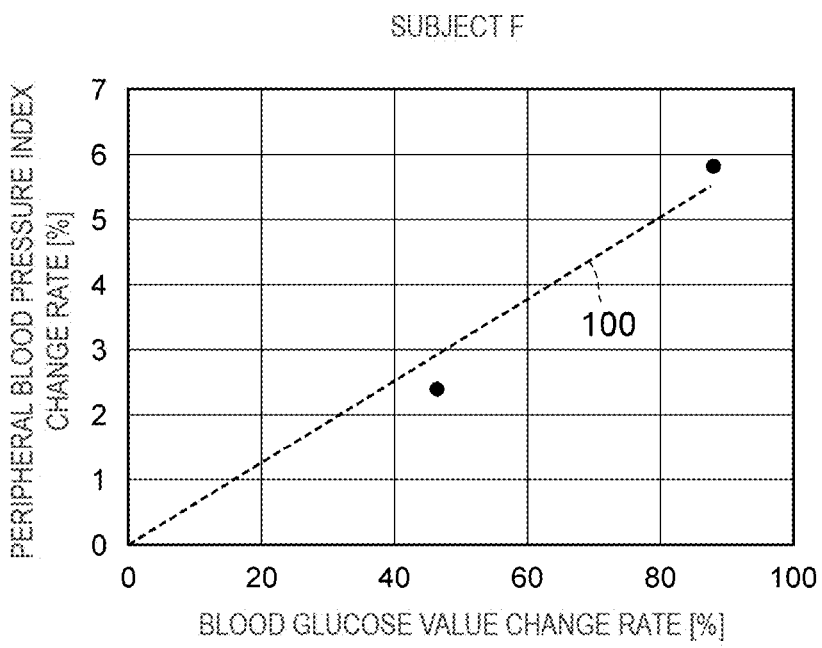
FIG. 12 is a graph showing a peripheral blood pressure index change rate with respect to a blood glucose value change rate in accordance with exemplary aspects of the present disclosure.

FIG. 12 shows a graph 100 of the peripheral blood pressure index change rate with respect to the blood glucose value change rate obtained by the regression analysis of the measurement points in a case where the same subject F undergoes the glucose tolerance test on different days. As shown in the graph 100, the peripheral blood pressure index change rate increases as the blood glucose value change rate increases, and thus the blood glucose value change rate is in a relationship of being substantially proportional to the peripheral blood pressure index change rate. The tendency of the change in the peripheral blood pressure index change rate with respect to the blood glucose value change rate is different between the graph 80 shown in FIG. 9 and the graph 100 shown in FIG. 12. As a cause of such a difference, it is presumed that there is no significant difference in the glucose metabolic capacity of the subject F, and the amounts of absorbed glucose are different from each other even though the subject takes the same amount of glucose on different days.

Figure 13:
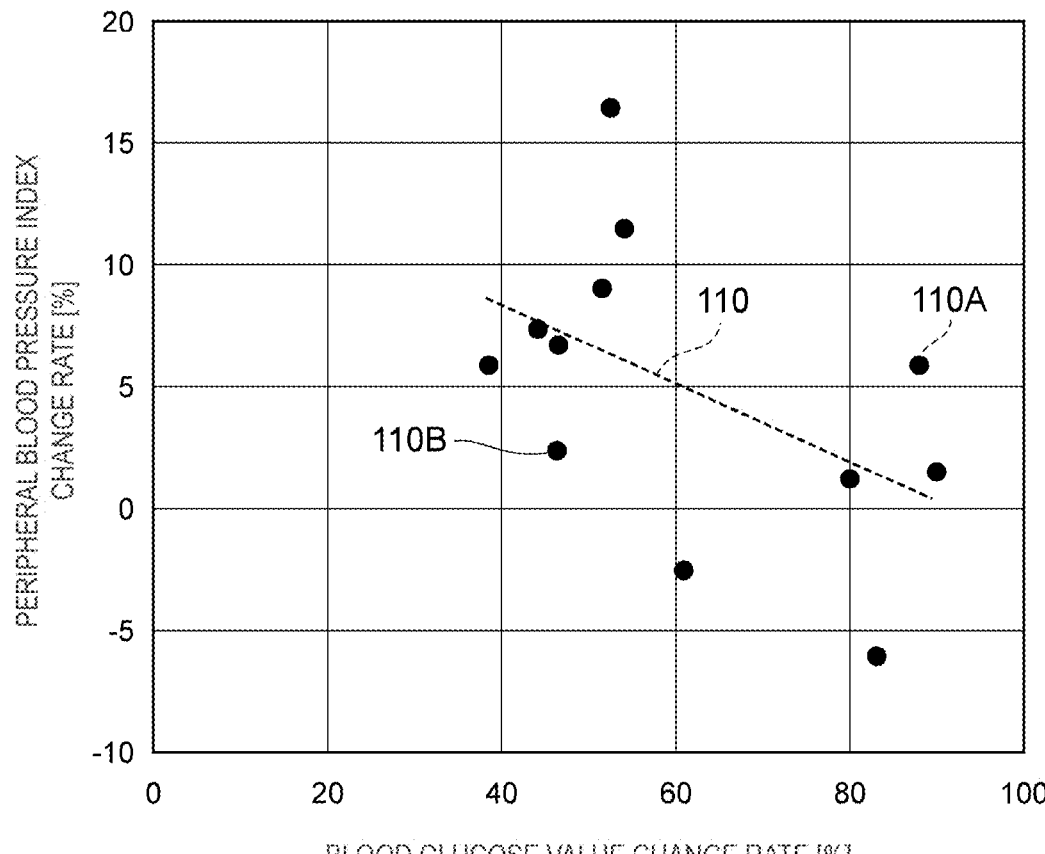
FIG. 13 is a graph showing a peripheral blood pressure index change rate with respect to a blood glucose value change rate in accordance with exemplary aspects of the present disclosure.

FIG. 13 shows a graph 110 of the peripheral blood pressure index change rate with respect to the blood glucose value change rate obtained by adding a measurement point 110A showing the measurement result of the first glucose tolerance test of the subject F (measurement result in a case where the subject F takes coffee) to the measurement results of FIG. 9 and performing the regression analysis on these measurement results. It is noted that a measurement point 110B shows the measurement result of the second glucose tolerance test of the subject F (measurement result in a case where the subject F does not take coffee). It is found that the coefficient of determination of the graph 110 shown in FIG. 13 is about 0.25, and the coefficient of determination is decreased from about 0.33 to about 0.25 by the addition of the measurement result in a case where the subject F takes coffee.

When the purpose of estimating the glucose metabolic capacity is to capture a sign of diabetes, a change should be captured on a monthly or yearly basis by excluding the influence of the physical condition of the subject during the test or the food and drink taken within a few hours. In the glucose tolerance test performed in a medical institution, the influence of intake of food and drink is excluded as much as possible by prohibiting the intake of food and drink for 10 hours or longer, but the influence of the physical condition cannot be excluded, and it is difficult to strictly carry out this type of glucose tolerance test in daily life except for the diagnosis in a hospital.

Figure 14:
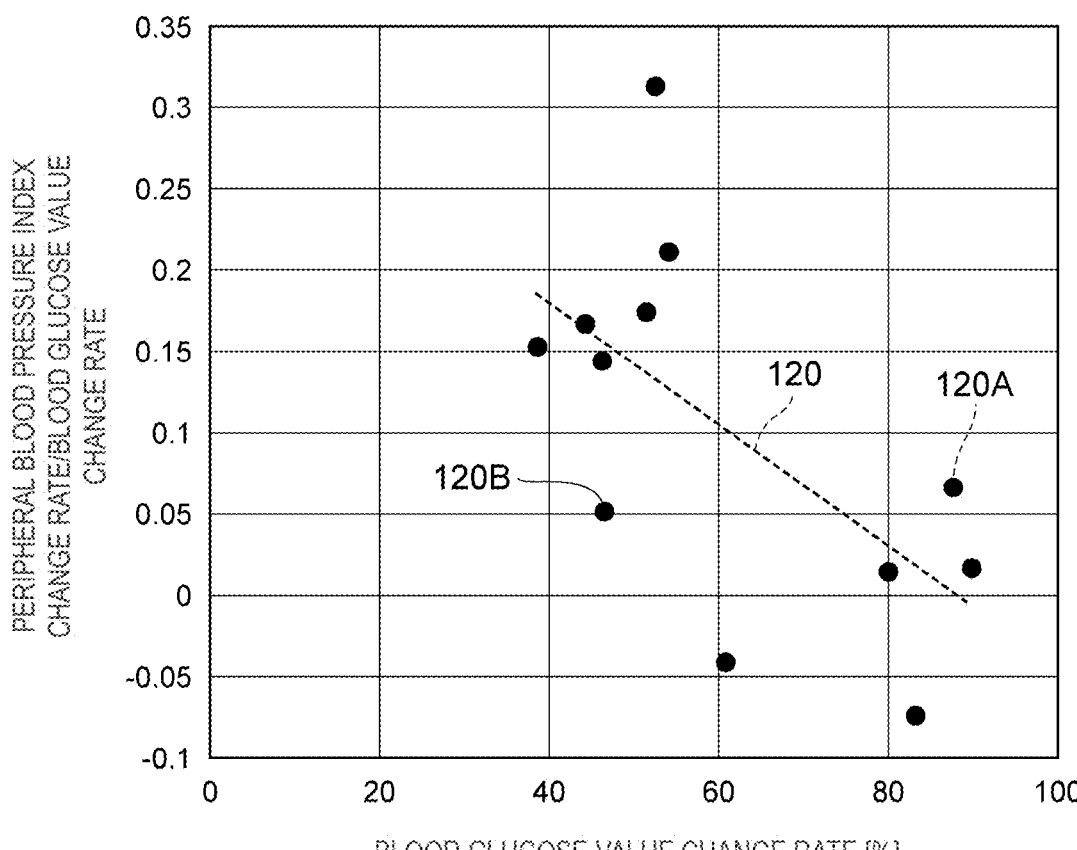
FIG. 14 is a graph showing a glucose metabolic capacity index with respect to a blood glucose value change rate in accordance with exemplary aspects of the present disclosure.

In view of the above-described circumstances, a new index is provided for a "peripheral blood pressure index change rate/blood glucose value change rate". It is considered that in a case where the new index is small (e.g., less than a predetermined value), this denotes that the peripheral blood pressure does not increase (or decrease) despite the large blood glucose value change rate and that the glucose metabolic capacity is decreased. FIG. 14 shows a graph 120 obtained by plotting, in place of the peripheral blood pressure index change rate, the new index with respect to the blood glucose value change rate and performing regression analysis on the plotted measurement points. The coefficient of determination of the graph 120 is about 0.38, and the correlation is improved as compared with the graph 110. It is noted that a measurement point 120A shows the measurement result of the first glucose tolerance test of the subject F (measurement point obtained by plotting, in place of the peripheral blood pressure index change rate, the new index described above with respect to the blood glucose value change rate). A measurement point 120B shows the measurement result of the second glucose tolerance test of the subject F (measurement point obtained by plotting, in place of the peripheral blood pressure index change rate, the new index described above with respect to the blood glucose value change rate).

However, as shown in the examples of FIGS. 10 to 12, the blood glucose value change rate is not necessarily appropriate as an index of the glucose metabolic capacity.

Therefore, the present disclosure considers "peripheral blood pressure index change rate/blood glucose value change rate" as an index showing the glucose metabolic capacity and thus proposes a method of estimating the index showing the glucose metabolic capacity. In the present specification, "peripheral blood pressure index change rate/blood glucose value change rate" is referred to as "glucose metabolic capacity index".

Figure 15:
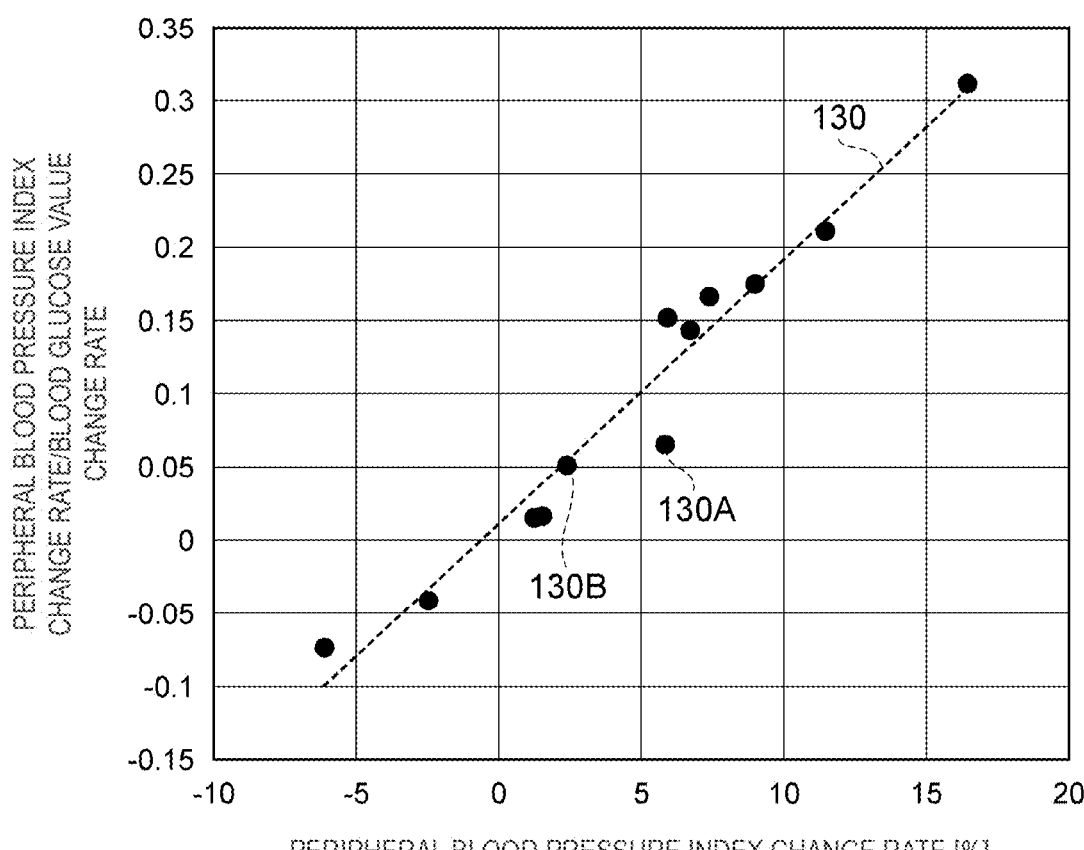
FIG. 15 is a graph showing a glucose metabolic capacity index with respect to a peripheral blood pressure index change rate in accordance with exemplary aspects of the present disclosure.

FIG. 15 shows a graph 130 of the glucose metabolic capacity index with respect to the peripheral blood pressure index change rate obtained by replacing the blood glucose value change rate of the measurement results shown in FIG. 14 with the peripheral blood pressure index change rate. It is noted that a measurement point 130A shows the measurement result of the first glucose tolerance test of the subject F (measurement result obtained by replacing the blood glucose value change rate of the measurement point 120A with the peripheral blood pressure index change rate). A measurement point 130B shows the measurement result of the second glucose tolerance test of the subject F (measurement result obtained by replacing the blood glucose value change rate of the measurement point 120B with the peripheral blood pressure index change rate).

The regression formula approximating the relationship between the peripheral blood pressure index change rate and the glucose metabolic capacity index can be first-order approximated, and the intercept thereof is close to 0. Therefore, the glucose metabolic capacity index can be determined from the peripheral blood pressure index change rate by determining the gradient of the regression formula of the graph 130 in advance. Further, since the gradient of the regression formula of the graph 130 can be regarded as a constant, the relationship between the peripheral blood pressure index change rate and the glucose metabolic capacity index has a one-to-one correspondence, and accordingly, the peripheral blood pressure index change rate can be treated as an index showing the glucose metabolic capacity.

The memory 322 of the signal processing device 32 stores in advance information (for example, information for determining a regression formula of the graph 130) for determining the relationship between the peripheral blood pressure index change rate and the glucose metabolic capacity index. When the processor 321 of the signal processing device 32 receives the measurement result of the sensing device 20 (for example, the pulse wave signal measured by the pulse wave sensor 211, the temperature value measured by the temperature sensor 212, and the movement acceleration of the sensing device 20 measured by the acceleration sensor 24), the processor 321 calculates the peripheral blood pressure index change rate from the pulse wave signal measured by the pulse wave sensor 211, and can estimate the glucose metabolic capacity index (that is, estimate the glucose metabolic capacity) based on the calculated peripheral blood pressure index change rate and the information stored in the memory 322 (that is, information for determining the relationship between the peripheral blood pressure index change rate and the glucose metabolic capacity index (for example, information for determining the regression formula of the graph 130)).

In the processing of estimating the glucose metabolic capacity index from the peripheral blood pressure index change rate, the change in the peripheral blood pressure index (for example, the maximum value of the peripheral blood pressure index change rate, the maximum value of the peripheral blood pressure index change amount, the peripheral blood pressure index change amount calculated by using $(t_i-t_{i-1}))/(t_n-t_0)$ in place of $(t_i-t_{i-1}))/(t_n-t_0)/X0$ in Calculation Formula (1), the dispersion of the peripheral blood pressure index change rate, the coefficient of variation, the time from the glucose tolerate having an extreme value, a change pattern, or the like) may be used in place of the peripheral blood pressure index change rate.

Further, information for determining the relationship between the blood flow rate index change rate and the glucose metabolic capacity index may be stored in advance in the memory 322 of the signal processing device 32. In a case where the processor 321 of the signal processing device 32 receives the measurement result of the sensing device 20 (for example, the pulse wave signal measured by the pulse wave sensor 211, the temperature value measured by the temperature sensor 212, the movement acceleration of the sensing device 20 measured by the acceleration sensor 24, or the like), the processor 321 calculates the blood flow rate index change rate from the pulse wave signal measured by the pulse wave sensor 211, and can estimate the glucose metabolic capacity index (that is, estimate the glucose metabolic capacity) based on the calculated blood flow rate index change rate and the information stored in the memory 322 (that is, the information for determining the relationship between the blood flow rate index change rate and the glucose metabolic capacity index.

In addition to the glucose tolerance test, the event that affects the blood glucose level of the user is a meal. The meal, different from the glucose tolerance test, cannot be controlled, because the kind of food materials, the amount thereof, the combination thereof, the meal time, and the time required for the meal will vary. Further, the intake of food and drink cannot be prohibited for 10 hours or longer before a meal. Therefore, it is difficult to estimate the glucose metabolic capacity in a case where only the blood glucose values before and after a meal are measured.

The glucose metabolic capacity index or the peripheral blood pressure index change rate before and after a meal is considered to be more suitable as an index for estimating the glucose metabolic capacity than the blood glucose value change rate, but it is still difficult to accurately estimate the glucose metabolic capacity in a case where the amount of glucose to be absorbed is small. Therefore, since the estimation accuracy of the glucose metabolic capacity may be low in a case where the peripheral blood pressure index change rate is measured only once, the estimation accuracy of the glucose metabolic capacity can be improved by determining the maximum value, the average value, the minimum value, the dispersion, the coefficient of variation, and the like of the peripheral blood pressure index change rate by using the measurement results of the peripheral blood pressure index change rate in a plurality of meals (for example, in units of one day or one week), and estimating the glucose metabolic capacity from these values.

In order to estimate the glucose metabolic capacity from the peripheral blood pressure index change rate before and after a meal, it may be necessary to determine whether the user is before the meal or after the meal. Examples of a method of distinguishing between before the meal and after the meal of the user include a method in which the user inputs before the meal or after the meal to the computer 30 at the measurement of the pulse wave signal and a method in which the computer 30 distinguishes between before the meal and after the meal based on the activity amount, the skin temperature, and the blood flow state of the user (for example, a method of determining that the user has taken a meal in a case where the pulse rate of the user has increased, the blood flow state has improved, and the skin temperature has increased even though the activity amount of the user has not increased).

The computer 30 can be configured to estimate the activity amount of the user from the movement acceleration of the sensing device 20 measured by the acceleration sensor 24. The blood flow state of the user can be estimated from, for example, the pulse wave feature quantity of the user. The blood flow state is correlated with the blood vessel age, and the blood vessel age can be estimated from the waveforms of the wave b and the wave d of the acceleration pulse wave signal. Therefore, the computer 30 can be configured to estimate the blood flow state using, for example, the pulse wave feature quantity of the wave b and the wave d. The computer 30 can then detect the skin temperature of the user from the measured temperature of the temperature sensor 212.

In addition, the biological information measurement system 10 can be configured to periodically measure the peripheral blood pressure index of the user without distinguishing between before the meal and after the meal of the user, calculate the dispersion, the coefficient of variation, and the like of the measurement result, estimate the capacity of the user to regulate the peripheral hemodynamics based on the calculation result, and estimate the glucose metabolic capacity of the user from the estimation result of the capacity of the user to regulate the peripheral hemodynamics. In this method, it may not be necessary to determine whether the user is before the meal or after the meal.

However, the peripheral hemodynamics of the user change according to the height of the measurement position (for example, a finger) from the heart. Therefore, it is desirable that the biological information measurement system 10 measures the peripheral blood pressure index of the user at a position where the height from the heart is constant, or corrects the peripheral blood pressure index in consideration of the deviation of the height of the measurement position (for example, a finger) from the heart.

The event that affects the blood glucose level of the user includes exercise in addition to the glucose tolerance test and the meal. The glucose metabolism increases and the blood flow rate also increases through exercise, particularly, anaerobic exercise. Although the increase depends on the exercise intensity and the environmental temperature, the increase in blood flow rate is typically greater than the increase after the intake of a meal, which is considered to be suitable for estimation of the glucose metabolic capacity. Since the blood flow rate is affected by the acceleration due to the exercise (for example, the blood flow rate of fingers increases or decreases in a case where the arm is shaken back and forth), it is desirable that the peripheral blood pressure index is measured in a resting state after the exercise.

In order to estimate the glucose metabolic capacity from the peripheral blood pressure index change rate before and after the exercise, it may be necessary to determine whether the user is before the exercise or after the exercise. Examples of a method of distinguishing between before the exercise and after the exercise of the user include a method in which the user inputs before the exercise or after the exercise to the computer 30 at the measurement of the pulse wave signal and a method in which the computer 30 distinguishes between before the exercise and after the exercise based on the activity amount of the user, the pulse rate, the skin temperature, and the blood flow state of the user (for example, a method of determining that the user has performed an exercise in a case where the activity amount of the user increases, the pulse rate of the user has increased, the blood flow state has improved, and the skin temperature has increased).

The event that affects the blood glucose level of the user includes sleep in addition to the glucose tolerance test, the meal, and the exercise. It is known that the blood flow rate also changes during sleep. In general, an increase in the peripheral blood flow during sleep leads to an increase in the peripheral skin temperature and a decrease in the deep body temperature, and it is said that the sleepiness increases as the peripheral skin temperature increases. Therefore, the change in the peripheral blood flow rate during sleep is related to the quality of sleep, and it can be presumed that the quality of sleep increases as the change in the peripheral blood flow rate during sleep increases. In addition, it can be presumed that the change in the peripheral blood pressure index during sleep decreases as the peripheral hemodynamic regulation capacity decreases.

However, since the change in the peripheral blood pressure index during sleep is affected by eating and drinking, bathing, the time elapsed from exercise, the environmental temperature, the physical condition, and the like in addition to the peripheral hemodynamic regulation capacity, the estimation accuracy of the peripheral hemodynamic regulation capacity is poor in a case of measurement for one day. Therefore, it is desirable to estimate the peripheral hemodynamic regulation capacity by determining the maximum value, the average value, the minimum value, the dispersion, the coefficient of variation, and the like of the change in the peripheral blood pressure index during sleep for a period of one day or longer, for example, for one week or one month. When the peripheral hemodynamic regulation capacity can be estimated, the glucose metabolic capacity can also be estimated as described above.

In order to estimate the glucose metabolic capacity from the peripheral blood pressure index change rate before and after sleep, it may be necessary to determine whether the user is before sleep or after sleep. Examples of a method of distinguishing between before sleep and after the sleep of the user include a method in which the user inputs before sleep or after sleep to the computer 30 at the measurement of the pulse wave signal and a method in which the computer 30 distinguishes between before sleep and after sleep based on a change in the activity amount of the user over time (for example, a method of determining that the user has fallen asleep in a case where the activity amount is decreased for a s time).

In order to improve the measurement accuracy of the change in the peripheral blood pressure index, examples of the factors that affect the peripheral blood pressure, which can be easily measured simultaneously with the measurement of the peripheral blood pressure, include the peripheral skin temperature, the outside air temperature, and autonomic nerve function.

The blood flow rate is affected by the outside air temperature, and thus the change in the blood flow rate is also affected by the outside air temperature. In a case in which the skin temperature is low or high, the change in the blood flow rate decreases, and the change in the peripheral blood pressure index also decreases. The estimation accuracy of the glucose metabolic capacity and the peripheral hemodynamic regulation capacity can be improved by estimating the influence of the outside air temperature from the peripheral skin temperature and correcting the peripheral blood pressure index.

Further, the same applies even in a case where the outside air temperature is used in place of the skin temperature, but the skin temperature varies greatly due to the influence of individual differences, the time spent in the environment, the clothes, the physical condition, and the like even in a case where the outside air temperature is the same, and the estimation accuracy of the skin temperature based on the outside air temperature is poor. Therefore, the correction accuracy of the peripheral blood pressure index decreases compared to a case of direct measurement of the skin temperature.

For example, when the height of the measurement position from the heart is low, the vascular resistance is substantially not changed, the peripheral blood pressure is increased, and the blood flow rate is increased. However, since the increase in the peripheral blood pressure is almost unrelated to the peripheral hemodynamic regulation capacity and the glucose metabolic capacity, the change in the peripheral blood pressure in such a case may be corrected by reducing the degree of contribution to the estimation of the peripheral hemodynamic regulation capacity and the glucose metabolic capacity.

The peripheral hemodynamics are also affected by the autonomic nerve function (the blood vessels contract in a case where the sympathetic nerve is activated), and thus the change in the peripheral blood pressure index is also affected by the autonomic nerve function. As a method of estimating the autonomic nerve function, a method using frequency analysis of heart rate (pulse rate) variation is well known. For example, in an extremely tense state, the sympathetic nerve may be activated, the heart rate may be increased, the heart rate variation may be decreased, and the hand may be cold. In such a case, the blood flow rate in the periphery decreases, the change in the blood flow rate also decreases, and the change in the peripheral blood pressure index also decreases. Such a temporary state may be corrected by reducing the degree of contribution to the estimation of the peripheral hemodynamic regulation capacity and the glucose metabolic capacity.

Figure 16:
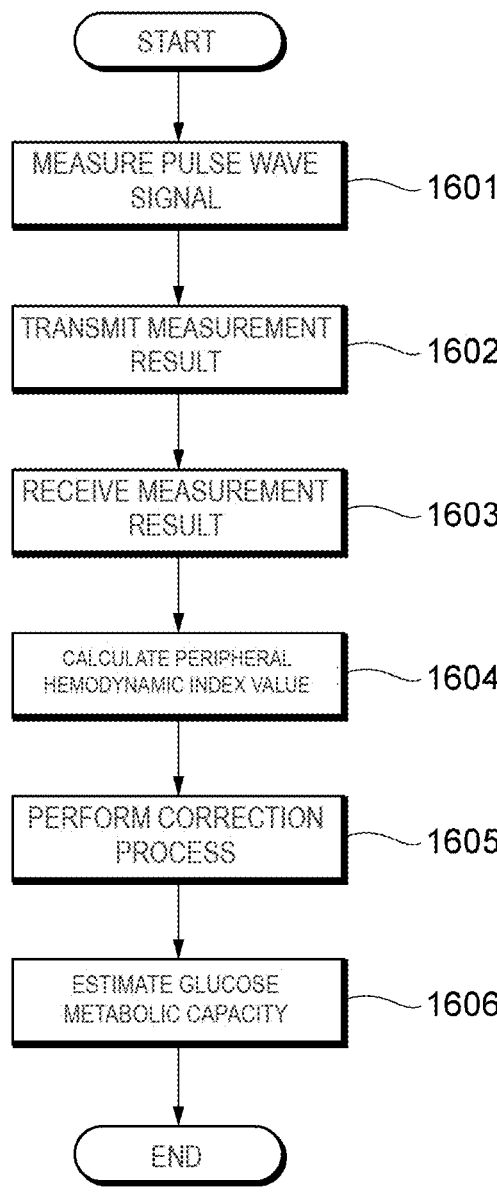
FIG. 16 is a flowchart illustrating a flow of processing in a method of estimating a glucose metabolic capacity in accordance with exemplary aspects of the present disclosure.

FIG. 16 is a flowchart illustrating a flow of processing in the method of estimating glucose metabolic capacity according to an aspect of the present disclosure.

In Step S1601, the pulse wave sensor 211 measures the pulse wave signal of the peripheral body part of the user before the event that affects the blood glucose level of the user (for example, the glucose tolerance test, meal, or exercise) and the pulse wave signal of the peripheral body part of the user after the event that affects the blood glucose level of the user (for example, the glucose tolerance test, meal, or exercise). In this case, the pulse wave sensor 211 may measure the pulse wave signal of the peripheral body part of the user at the measurement position where the height from the heart of the user is the same. The temperature sensor 212 measures the skin temperature of the peripheral body part of the user. The acceleration sensor 24 measures the movement acceleration of the sensing device 20.

In Step S1602, the sensing device 20 transmits the measurement results of the sensing device 20 (for example, the pulse wave signal measured by the pulse wave sensor 211, the temperature value measured by the temperature sensor 212, and the movement acceleration of the sensing device 20 measured by the acceleration sensor 24) to the computer 30.

In Step S1603, the computer 30 receives the measurement results of the sensing device 20.

In Step S1604, the computer 30 calculates the peripheral hemodynamic index value of the user. For example, the computer 30 calculates the pulse wave feature quantity from the pulse wave signal measured by the pulse wave sensor 211 and calculates the peripheral hemodynamic index value of the user from the calculated pulse wave feature quantity.

As described above, the measuring of the peripheral hemodynamic index value of the user includes Step S1601 of measuring the pulse wave signal, Step S1602 of transmitting the measurement results of the pulse wave signal, Step S1603 of receiving the measurement results of the pulse wave signal, and Step S1604 of calculating the peripheral hemodynamic index value from the pulse wave signal.

In Step S1605, the computer 30 performs a correction process of the peripheral hemodynamic index value of the user.

For example, the computer 30 may correct the peripheral hemodynamic index value according to the skin temperature measured by the temperature sensor 212.

For example, the computer 30 may estimate the pulse interval by determining the variation period from the pulse wave signal measured by the pulse wave sensor 211, may calculate the index value of the autonomic nerve function by performing power spectrum analysis on the frequency component of the periodic variation of the heartbeat from the estimated pulse interval, and may correct the peripheral hemodynamic index value according to the index value of the autonomic nerve function.

In Step S1606, the computer 30 estimates the glucose metabolic capacity of the user from a change in an index value indicating the peripheral blood pressure of the user, which is measured before and after the event that affects the blood glucose level of the user (for example, the peripheral blood pressure index change rate, the maximum value of the peripheral blood pressure index change rate, the maximum value of the peripheral blood pressure index change amount, the peripheral blood pressure index change amount calculated by using $(t_i-t_{i-1}))/(t_n-t_0)$ in place of $(t_i-t_{i-1}))/(t_n-t_0)/X0$ in Calculation Formula (1), the dispersion of the peripheral blood pressure index change rate, the coefficient of variation, the time from the glucose tolerate having an extreme value, a change pattern, and the like) or a change in an index value indicating the peripheral blood flow rate. For example, when the change in the peripheral blood flow rate of the user or the change in the peripheral blood pressure of the user is small (e.g., less than a predetermined value), the computer 30 can be configured to determine that the glucose metabolic capacity of the user is low.

In Step S1601, the pulse wave sensor 211 may measure the pulse wave signal of the peripheral body part of the user a plurality of times continuously or intermittently from before the event that affects the blood glucose level of the user (for example, the glucose tolerance test, meal, or exercise) to after the event that affects the blood glucose level of the user (for example, glucose tolerance test, meal, or exercise).

Further, in the description above, any of the glucose tolerance test, the meal, or the exercise has been exemplified as the event that affects the blood glucose level of the user, but the event that affects the blood glucose level of the user may be sleep.

When the event that affects the blood glucose level of the user is sleep, the pulse wave sensor 211 may measure the pulse wave signal of the peripheral body part of the user during the sleep of the user a plurality of times continuously or intermittently in Step S1601. Further, in Step S1606, the computer 30 may estimate the glucose metabolic capacity, the peripheral hemodynamic regulation capacity, or the quality of sleep of the user based on the change in the peripheral hemodynamic index value measured during the sleep of the user.

It is noted that the processes in Steps S1602 to S1605 in a case where the event that affects the blood glucose level of the user is the sleep are the same as the processes in Steps S1602 to S1605 in a case where the event that affects the blood glucose level of the user is any of the glucose tolerance test, the meal, or the exercise.

Further, in the description of the exemplary aspects above, the method of estimating the glucose metabolic capacity of the user from the change in the peripheral hemodynamic index value of the user has been described, but the present disclosure is not limited to this. For example, the biological information measurement system 10 may measure the peripheral hemodynamic index value and the blood glucose value of the user before and after the event that affects the blood glucose level of the user, and may estimate the glucose metabolic capacity of the user from the change in the peripheral hemodynamic index value and the change in the blood glucose value, which are measured before and after the event that affects the blood glucose level of the user. The easiness of absorption of glucose changes depending on the kind of the food materials consumed, the amount thereof, the food combination, the physical condition, and the like, and in a case where the amount of absorbed glucose is not known, the glucose metabolic capacity is not known accurately. The glucose metabolic capacity can be accurately estimated by measuring the blood glucose value and the peripheral hemodynamic index value at the same time.

It is also noted that the computer 30 can be configured to determine the blood glucose value by calculation based on the pulse wave signal measured by the pulse wave sensor 211. In addition, when the glucose metabolic capacity of the user is estimated from the change in the peripheral hemodynamic index value and the change in the blood glucose value which are measured before and after the event that affects the blood glucose level of the user, the information for determining the relationship between the peripheral blood pressure index change rate and the glucose metabolic capacity index (for example, information for determining the regression formula of the graph 130) may not be necessary.

According to an aspect of the present disclosure, the glucose metabolic capacity can be estimated in a non-invasive and simple manner by measuring the pulse wave signal using the pulse wave sensor 211.

Further, the change in the peripheral hemodynamics after the event that affects the blood glucose level of the user occurs in about 0 to 2 hours, but the change pattern is not constant due to individual differences or the like. A pattern of the change in the peripheral hemodynamics can be grasped by measuring the pulse wave signal a plurality of times during this time period, and thus the accuracy of estimating the glucose metabolic capacity can be improved.

Further, since the amount of glucose intake varies depending on the food materials and the amount thereof, it is difficult to determine the glucose metabolic capacity in a single measurement before and after a meal. However, the glucose metabolic capacity can be more accurately estimated by measuring the change in the peripheral hemodynamic index after meal a plurality of times.

In addition, there is no event that significantly affects the blood glucose level (for example, the glucose tolerance test, meal, or exercise) during sleep, but typically, the blood flow rate to the brain decreases and the blood flow rate to the peripheral blood vessels increases. The glucose metabolic capacity can be estimated from this change in the peripheral hemodynamics.

In addition, since the peripheral hemodynamics are affected by the outside air temperature, the change in the peripheral hemodynamic index is also affected by the outside air temperature. The estimation accuracy of the glucose metabolic capacity and the peripheral hemodynamic regulation capacity can be improved by estimating the influence of the outside air temperature from the skin temperature and correcting the peripheral hemodynamic index.

In addition, since the peripheral hemodynamics are affected by the autonomic nerve function (for example, blood vessel constriction occurs due to sympathetic nerve activation, and a decrease in blood flow rate is caused), the change in the peripheral hemodynamics is also affected by the autonomic nerve function. The estimation accuracy of the glucose metabolic capacity and the peripheral hemodynamic regulation capacity can be improved by analyzing the autonomic nerve function from the pulse interval variation and correcting the change in the peripheral hemodynamic index based on the result.

It is noted that the pulse wave sensor 211 has an advantage that the sensor is small (in size) and can be mounted on a finger, a wrist, an ear, or the like, and thus can be incorporated into a wearable device. Examples of the wearable device include a wristband-type device mounted on a wrist, a wristwatch-type device, an earphone-type device mounted on an ear, and a patch-type device mounted the skin in addition to a ring-type device mounted on a finger of the user. Further, the sensing device 20 is not necessarily a wearable device, and may be, for example, a portable device (for example, a multifunctional mobile phone called a smartphone) or a stationary device having a configuration in which the pulse wave signal is measured by placing a finger on a pulse wave sensor.

In an exemplary aspect, a laser Doppler blood flow meter or an ultrasonic Doppler blood flow meter may be used instead of the pulse wave sensor 211. The laser Doppler blood flow meter can be reduced in size and has satisfactory measurement accuracy, but the ultrasonic Doppler blood flow meter is difficult to be reduced in size and has poor measurement accuracy as compared with the laser Doppler blood flow meter. According to the method of determining, by calculation, the peripheral hemodynamic index from the pulse wave feature quantity of the pulse wave signal measured by the pulse wave sensor 211, the sensing device 20 can be reduced in size and is suitable for cost reduction.

In addition, the laser Doppler blood flow meter has satisfactory accuracy in measuring the blood flow velocity, but is easily affected by the contact state with the skin, the pressing, and the like in measuring the blood flow rate. Meanwhile, a method of estimation from the feature quantity of the photoplethysmographic waveform is also affected by the contact state with the skin, the pressing, and the like, but the influence can be reduced by selecting the feature quantity to be used. For example, in a case where the pulse wave amplitude is employed as the feature quantity, the influence is strong, but the estimation method is less likely to be affected in a case where the feature quantity such as the peak time of the pulse wave waveform is used. Therefore, the stability and reproducibility of the estimation of the peripheral hemodynamics can be improved by selecting a suitable feature quantity.

It is generally noted that the exemplary aspects described above are to facilitate the understanding of the present disclosure, and are not intended to limit the present disclosure. The present disclosure can be changed or improved without departing from the spirit of the present disclosure, and the present disclosure includes equivalents thereof. That is, even a modification made by those skilled in the art to the aspects as appropriate is included in the scope of the present disclosure as long as the modification has the features of the present disclosure. In addition, respective elements provided in the aspects can be combined with each other as technically possible, and a combination thereof is also included in the scope of the present disclosure as long as the combination has the features of the present disclosure.

REFERENCE SIGNS LIST 10 biological information measurement system, 20 sensing device, 21 biosensor, 22 control circuit, 23 communication module, 24 acceleration sensor, 25 housing, 211 pulse wave sensor, 212 temperature sensor, 30 computer, 31 communication module, 32 signal processing device, 321 processor, 322 memory, 323 input/output interface, 40 user, 41 heart.

The invention claimed is:

1. A method executed by a biological information measurement system, the method comprising:

before an event that affects a blood glucose level of a user, calculating a first peripheral hemodynamic index value of the user based on a pulse wave feature quantity determined from a pulse wave signal measured by a pulse wave sensor, the pulse wave feature quantity being at least one of a peak time differences of respective peaks, a height of each peak, a ratio of a peak time difference of each peak to a pulse interval, a peak half width, a ratio between an area on a positive side and an area on a negative side of an acceleration pulse wave signal;

after the event that affects the blood glucose level of the user, calculating a second peripheral hemodynamic index value of the user based on the pulse wave feature quantity determined from the pulse wave signal measured by the pulse wave sensor; and estimating a glucose metabolic capacity of the user based on a change between the first peripheral hemodynamic index value and the second peripheral hemodynamic index value.

2. The method according to claim 1, wherein calculating the first peripheral hemodynamic index value and calculating the second peripheral hemodynamic index value includes calculating at a plurality of times continuously or intermittently from before the event to after the event.

3. The method according to claim 1, further comprising determining that the user has a low glucose metabolic capacity when the change between the first peripheral hemodynamic index value and the second peripheral hemodynamic index value of the user is below a given value in mg/dL.

4. The method according to claim 1, wherein calculating the first peripheral hemodynamic index value of the user and calculating the second peripheral hemodynamic index value of the user includes measuring the user at a measurement position where a height from a heart of the user is identical.

5. The method according to claim 1, further comprising:

measuring a skin temperature of a peripheral body part of the user; and correcting the first peripheral hemodynamic index value or the second peripheral hemodynamic index value of the user according to the skin temperature.

6. The method according to claim 1, further comprising:

estimating a pulse interval of the user;

calculating an index value of an autonomic nerve function of the user from a variation of the pulse interval; and correcting the first peripheral hemodynamic index value of the user or the second peripheral hemodynamic index value of the user according to the index value of the autonomic nerve function.

7. The method according to claim 1, further comprising:

measuring a photoplethysmographic signal at a peripheral body part of the user; and calculating the first peripheral hemodynamic index value of the user or the second peripheral hemodynamic index value of the user from a feature quantity of the photoplethysmographic signal.

8. The method according to claim 1, further comprising:

before the event that affects the blood glucose level of the user, measuring a first blood glucose value of the user;

after the event that affects the blood glucose level of the user, measuring a second blood glucose value of the user; and estimating a glucose metabolic capacity of the user based on the change between the first peripheral hemodynamic index value and the second peripheral hemodynamic index value, and a change between the first blood glucose value and the second blood glucose value.

*　　*　　*　　*　　*